US010952918B2

(12) United States Patent
Palmer

(10) Patent No.: US 10,952,918 B2
(45) Date of Patent: Mar. 23, 2021

(54) NEONATAL CHEST SPLINT FOR APPLYING NEGATIVE DISTENDING PRESSURE

(71) Applicant: The Penn State Research Foundation, University Park, PA (US)

(72) Inventor: Charles Palmer, Hummelstown, PA (US)

(73) Assignee: The Penn State Research Foundation, University Park, PA (US)

(*) Notice: Subject to any disclaimer, the term of this patent is extended or adjusted under 35 U.S.C. 154(b) by 678 days.

(21) Appl. No.: 15/287,859

(22) Filed: Oct. 7, 2016

(65) Prior Publication Data
US 2017/0020768 A1    Jan. 26, 2017

Related U.S. Application Data

(63) Continuation-in-part of application No. PCT/US2015/024472, filed on Apr. 6, 2015.

(60) Provisional application No. 61/976,095, filed on Apr. 7, 2014.

(51) Int. Cl.
*A61H 9/00* (2006.01)
*A61H 31/02* (2006.01)
*A61F 5/32* (2006.01)
*A61F 5/34* (2006.01)

(52) U.S. Cl.
CPC .............. *A61H 9/0007* (2013.01); *A61F 5/32* (2013.01); *A61F 5/34* (2013.01); *A61H 9/0078* (2013.01); *A61H 31/02* (2013.01); *A61H 2201/165* (2013.01); *A61H 2205/084* (2013.01)

(58) Field of Classification Search
CPC ...... A61H 9/0078; A61H 31/02; A61H 31/00; A61H 2205/084; A61H 2201/165; A61H 2201/1635; A61H 9/005–0092; A61F 5/34; A61F 5/32
USPC .................................... 601/41, 44, 106, 151
See application file for complete search history.

(56) References Cited

U.S. PATENT DOCUMENTS

| 2,529,258 | A |   | 11/1950 | Lobo |   |
|---|---|---|---|---|---|
| 2,869,537 | A | * | 1/1959 | Jen-Chu | A61H 9/0078 482/112 |
| 4,355,632 | A | * | 10/1982 | Sandman | A61F 5/34 601/152 |
| 4,960,118 | A |   | 10/1990 | Pennock |   |

(Continued)

*Primary Examiner* — Tu A Vo
*Assistant Examiner* — Alexander Morales
(74) *Attorney, Agent, or Firm* — Riverside Law LLP

(57) ABSTRACT

The present invention relates to devices and methods for assisting breathing in a subject. In one embodiment, the device of the present invention is a splint that can be used to apply negative distending pressure, i.e., outward pull, to one or both of the chest walls and/or the abdomen of a subject. In certain embodiments, the splint comprises an air bladder that can be attached to the skin of the subject's chest and/or abdomen. When the air bladder is inflated, negative distending pressure is applied to the subject's chest and/or abdomen, thereby assisting or promoting respiration. In another embodiment, the splint comprises a piezoelectric material that when activated can provide negative distending pressure to the subject's chest and/or abdomen. In another embodiment, the subject is a neonate. In another embodiment, the inflated air bladder can apply a compressive force on the chest to facilitate expiration, and the removal of secretions in the airways.

43 Claims, 10 Drawing Sheets

(56) References Cited

U.S. PATENT DOCUMENTS

| | | | |
|---|---|---|---|
| 5,555,880 A * | 9/1996 | Winter | A61M 16/0096 |
| | | | 128/204.21 |
| 5,738,089 A | 4/1998 | Hoshi | |
| 5,911,612 A * | 6/1999 | Steger | B63C 9/1255 |
| | | | 441/116 |
| 6,059,742 A | 5/2000 | Palmer | |
| 6,533,739 B1 | 3/2003 | Palmer | |
| 6,700,031 B1 * | 3/2004 | Hahn | A61H 7/001 |
| | | | 601/134 |
| 6,736,785 B1 | 5/2004 | Van Brunt | |
| 6,796,875 B1 | 9/2004 | Placik | |
| 8,764,689 B2 * | 7/2014 | Toth | A61H 23/0254 |
| | | | 601/134 |
| 2005/0072470 A1 | 4/2005 | Jacobs | |
| 2005/0075531 A1 * | 4/2005 | Loeb | A61H 9/0078 |
| | | | 600/17 |
| 2005/0267387 A1 * | 12/2005 | Baldauf | A61H 31/02 |
| | | | 601/44 |
| 2008/0195018 A1 * | 8/2008 | Larson | A61B 17/1325 |
| | | | 602/53 |
| 2014/0276271 A1 * | 9/2014 | Stryker | A61H 23/04 |
| | | | 601/46 |
| 2015/0272822 A1 * | 10/2015 | Wik | A61M 16/0096 |
| | | | 128/204.21 |

\* cited by examiner

NEONATAL CHEST SPLINT FOR APPLYING NEGATIVE DISTENDING PRESSURE

CROSS-REFERENCE TO RELATED APPLICATIONS

This application is a continuation-in-part of PCT Patent Application No. PCT/US15/24472, filed Apr. 6, 2015, which claims priority to U.S. Patent Application Ser. No. 61/976,095, filed Apr. 7, 2014, the entire contents of which are both incorporated herein by reference in their entireties.

BACKGROUND OF THE INVENTION

Newborn babies, especially those born prematurely, can experience a range of breathing issues immediately after being born. Premature infants with respiratory distress have stiff lungs and a compliant chest wall. The soft rib cage and compliant chest wall in neonates can result in the chest wall readily collapsing during spontaneous respiration. Further, neonates often have to do extra work in breathing to overcome the chest wall retraction, and the lack of chest wall rigidity allows the lung to collapse. A collapsed lung is more difficult for the neonate to inflate. Therefore, premature infants often require assistance to maintain adequate lung volumes. This is achieved by providing mechanical ventilation or continuous distending pressure.

A number of methods and devices for assisting neonatal breathing are known in the art. For example, continuous positive airway pressure (CPAP) can be an effective method for assisting breathing, preventing chest wall collapse, and providing distending pressure. However, CPAP can have major side-effects, such as airway drying and obstruction of nasal passages, and the erosion of the nasal septum from pressure necrosis. Even when positive distending pressure is applied non-invasively, i.e., without endotracheal intubation, it fails to support spontaneous respiration in 30-50% of preterm infants with respiratory distress. These infants are then intubated, given surfactant and mechanically ventilated. Mechanical ventilation via an endotracheal tube is associated with injury to the lung and chronic lung disease. Further, chronic lung disease is associated with neurodevelopmental impairment. Accordingly, clinicians caring for preterm infants with respiratory distress prefer to support spontaneous respiration without the need for intubation and mechanical ventilation. In addition, the cost of surfactant is prohibitive in some countries. Therefore, non-invasive ventilation of a neonate, for example the application of negative distending pressure, is preferred over intubation and positive pressure ventilation.

Methods and devices for applying negative distending pressure known in the art include the neonatal chest brace described by Palmer et al. (U.S. Pat. No. 6,533,739). While the chest brace in Palmer represents a notable advancement in the field, it is not suitable for certain applications, because it requires a rigid brace that can interfere with the delicate condition of most neonates, especially those born prematurely. Specifically, in certain applications the rigid brace is not sufficiently flexible for applying delicate adjustments to the negative distending pressure in a neonate. The infants that fail non-invasive ventilation with CPAP are typically the smallest and most immature, for example those weighing less than 1000 grams. The chest brace in Palmer is not suitable for these infants, who require a more delicate means of negative distension. The chest brace is also mechanically complicated and is not easily applied. Most importantly, the chest brace does not permit active ventilation of the neonate and it does not permit oscillation of the chest wall.

Thus, there is a continuing need in the art for applying negative distending pressure to a neonate in need of respiratory assistance for the purposes of 1) stabilizing the chest wall, preventing chest wall retractions and collapse of the lung, and 2) to providing active negative pressure ventilation. The present invention addresses this continuing need in the art.

SUMMARY

In one embodiment, a splint for assisting breathing in a subject includes a first flexible cuff having an inflatable compartment, a tube connected to the inflatable compartment of the first cuff, wherein the tube is suitable for delivery or removal of air from the compartment; and an attachment mechanism for releasably engaging the first cuff to a region of the subject's chest or abdomen, where when the first cuff is attached to a chest or abdomen of the subject and a posterolateral or posterior region of the subject via the attachment mechanism and the compartment is inflated, a portion of the first cuff is extended, thereby applying negative distending pressure to the subject's chest or abdomen. In one embodiment, the splint includes a second flexible cuff having an inflatable compartment, a tube connected to the inflatable compartment of the second cuff, wherein the tube is suitable for delivery or removal of air from the compartment; and an attachment mechanism for releasably engaging the second cuff to a region of the subject's chest or abdomen, where when the second cuff is attached to a chest or abdomen of the subject and a posterolateral or posterior region of the subject via the attachment mechanism and the compartment is inflated, a portion of the second cuff is extended, thereby applying negative distending pressure to the subject's chest or abdomen. In one embodiment, the first cuff is configured for attachment to a left side of the subject, and wherein the second cuff is configured for attachment to a right side of the subject. In one embodiment, both the first and second cuffs are configured for attachment to the same side of the subject. In one embodiment, a system includes a first and second splint, where a first pair of cuffs on the first splint are designated for attachment to the chest of the subject, and wherein a second pair of cuffs on the second splint is designated for attachment to the abdomen of the subject. In one embodiment, the system includes a controller operably connected to the first cuff and the second cuff. In one embodiment, the system includes at least one sensor; where the controller is configured to change operation of the first and second pairs of cuffs based on feedback detected from the at least one sensor. In one embodiment, the change in operation is at least one of synchronization, displacement, or an on/off operational state. In one embodiment, the splint includes a second, third and fourth flexible cuff each including a flexible cuff having an inflatable compartment, a tube connected to the inflatable compartment of the cuff, wherein the tube is suitable for delivery or removal of air from the compartment; and an attachment mechanism for releasably engaging the cuff to a region of the subject's chest or abdomen, where when the cuffs are attached to a chest and abdomen of the subject and a posterolateral or posterior region of the subject via the attachment mechanism and the compartment is inflated, a portion of the first cuff is extended, thereby applying negative distending pressure to the subject's chest and abdomen. In one embodiment, the splint is flexible and substantially inelastic. In one embodiment, the attachment mechanism comprises one or more fastening strips, a means for attaching the one or more fastening strips to the subject's skin, and a means for attaching the one or more fastening strips to the cuff. In one embodiment, the means for attaching the one or more fastening strips to the cuff is a hook and loop fastener. In one embodiment, the means for attaching the one or more fastening strips to the subject's skin is a hydrogel or a hydrocolloid dressing, or other skin protective layer like a semipermeable membrane. In one embodiment, the compartment is inflated by transferring air to the compartment via a syringe or a bulb syringe. In one embodiment, the compartment is inflated by transferring air to the compartment via a ventilator or an air pump. In one embodiment, the subject's sternum is not covered by the cuff when the splint is attached to the subject. In one embodiment, at least a portion of a surface of the cuff comprises a soft fabric. In one embodiment, the subject is a neonate.

A method for assisting breathing in a subject includes the steps of attaching at least one cuff having an inflatable compartment to the chest or abdomen and a posterolateral or posterior region of a subject; inflating the at least one cuff by transferring air into the compartment; and applying a negative distending pressure to the subject's chest or abdomen via the inflating. In one embodiment, the method includes the step of at least partially deflating the at least one cuff to reduce the negative distending pressure applied to the subject's chest or abdomen. In one embodiment, at least a portion of the subject's chest or abdomen is not covered by the at least one cuff. In one embodiment, the at least a portion of the subject's chest or abdomen comprises the subject's sternum. In one embodiment, the at least one cuff is attached to the subject's chest or abdomen by a skin attachment mechanism. In one embodiment, the skin attachment mechanism is a hydrogel. In one embodiment, the skin attachment mechanism is a hydrocolloid. In one embodiment, the skin attachment mechanism is a semi-permeable membrane dressing. In one embodiment, air is transferred into the compartment via a syringe or a bulb syringe. In one embodiment, air is transferred into the compartment via a ventilator or an air pump. In one embodiment, a predetermined amount of air is transferred into the compartment to inflate the at least one cuff. In one embodiment, the predetermined amount of air corresponds to an application of negative distending pressure to the subject's chest or abdomen that causes the subject to inhale a breath approximately equal to or less than the tidal volume. In one embodiment, the inflation of the at least one cuff is synchronized with the spontaneous inspiration of the subject. In one embodiment, the negative distending pressure applied to the subject's chest or abdomen is maintained for a predetermined period of time. In one embodiment, the method includes the step of deflating the at least one cuff to release the negative distending pressure. In one embodiment, the inflating or deflating of the at least one cuff occurs at high frequency (2-15 Hz) and is controlled via a high frequency generator of air pressure as is found in a high frequency oscillator or a high frequency jet ventilator. In one embodiment, the inflating or deflating of the at least one cuff is controlled based on the activity of the subject's diaphragm. In one embodiment, the air is transferred into the compartment via a column of bubbling water set to an adjustable depth to regulate the pressure delivered to the cuff. In one embodiment, the method includes the step of attaching the at least one cuff to the left side of the subject's chest and attaching a second cuff to the right side of the subject's chest. In one embodiment, the method includes the step of attaching the at least one cuff to the left side of the subject's abdomen and attaching a second cuff to the right side of the subject's abdomen. In one embodiment, the method includes the step of attaching the at least one cuff to the subject's chest and attaching a second cuff to the to the subject's abdomen, wherein both the at least one cuff and the second cuff are on the same side of the subject. In one embodiment, the method includes the steps of attaching the at least one cuff and a second cuff to the subject's chest; and attaching a third and fourth cuff to the subject's abdomen. In one embodiment, the operation of the at least one cuff is based on sensor feedback.

In one embodiment, a method for assisting exhalation of breathing in a subject comprising the steps of attaching a cuff having an inflatable compartment to the chest or abdomen of a subject, wherein the cuff is continuous over the anterior portion of the subject's chest or abdomen, and inflating the cuff by transferring air into the compartment, wherein when the inflatable compartment of the cuff is inflated the cuff compresses the chest and/or abdomen.

In one embodiment, a device for assisting breathing in a subject comprises a flexible cuff, comprising a piezoelectric material, and an attachment mechanism for releasably engaging the cuff to a region of a subject's chest or abdomen and a region of the subject's back, wherein when the cuff is attached to the subject's chest or abdomen and back via the attachment mechanism and the piezoelectric material is activated by applying an electrical signal to the piezoelectric material, a portion of the cuff is extended, thereby applying negative distending pressure to the subject's chest or abdomen.

BRIEF DESCRIPTION OF THE DRAWINGS

The following detailed description of various embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
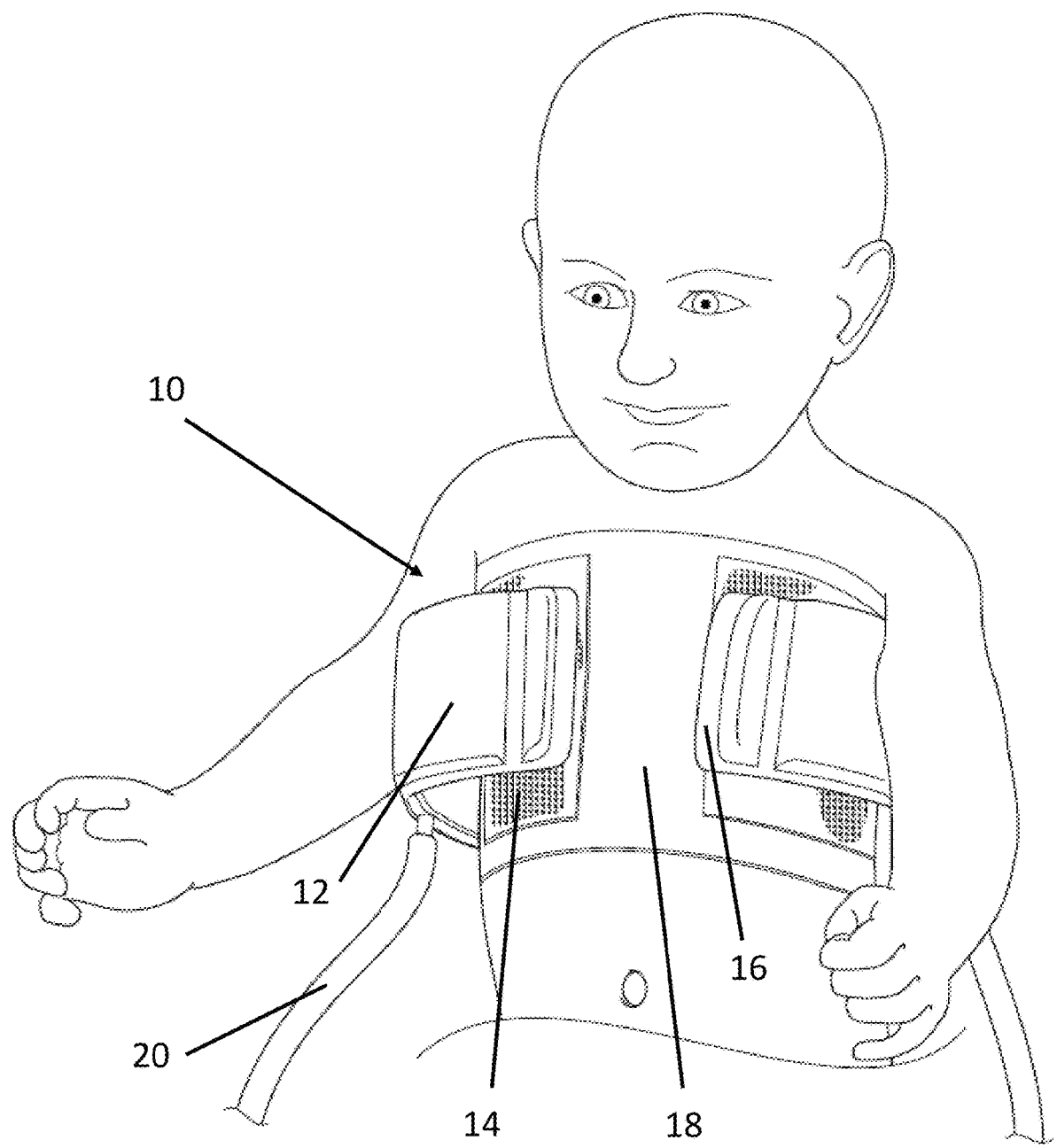
FIG. 1 is a diagram of an exemplary embodiment of the device of the present invention connected to a patient, showing an anterior view.

It is to be understood that the figures and descriptions of the present invention have been simplified to illustrate elements that are relevant for a clear understanding of the present invention, while eliminating, for the purpose of clarity, many other elements found in ventilation devices and methods of breathing assistance. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments there between. This applies regardless of the breadth of the range.

DESCRIPTION

The present invention relates to devices and methods for assisting breathing in a patient. In a preferred embodiment, the patient is a neonate. In other embodiments, the devices and methods of the present invention can be applied to more mature patients who have a flail anterior chest wall, for example a patient suffering from trauma to the chest or a patient having a chest wall that is not mineralized. In one embodiment, the device of the present invention is a flexible yet non-elastic splint that conforms in part to the shape of the subject's thorax, and can be used to apply negative distending pressure to the compliant chest wall of a neonate. In such an embodiment, the splint comprises an air bladder that is configured to cover a portion of a newborn's chest and a mechanism for attaching the air bladder to the newborn's chest. When the air bladder is inflated, the splint can provide negative distending pressure, i.e., outward pull, to the newborn's chest. When the lungs in the chest are exposed to a surrounding negative pressure (less than atmospheric pressure) they expand as air flows down a pressure gradient from the mouth into the lung. Accordingly, in one embodiment, the breathing of the newborn can be assisted by inflating and deflating the air bladder intermittently, i.e., via cycles or oscillations of distending pressure applied to the cuff which in turn generates a negative distending pressure in newborn's chest. In another embodiment, the newborn's breathing can be assisted by maintaining constant inflation of the air bladder, for example in newborns with chest wall collapse and retractions.

The device of the present invention presents a number of significant and unexpected improvements over existing devices. For example, it reduces or eliminates the need for rigid components that can interfere with the creation of distending pressure, and can cause the device to be complicated to use and/or time-consuming to set up. Further, in certain embodiments the splint of the present invention does not completely encircle the patient's chest or thoracic region, and thus allows for the level of delicacy and access required in neonatal care. In a preferred embodiment, the cuff can be applied to the antero-lateral aspects of the chest, leaving the middle part of the chest, the area over the sternum uncovered. Accordingly, the device permits easier access for ultrasound evaluation of the heart, i.e., echocardiography, than devices currently available. In another embodiment, the device permits negative pressure ventilation as well as negative pressure distention and reduction of chest wall deformation.

In addition, the device of the present invention can be attached to multiple areas of the patient's chest wall, including areas other than the sternum. For example, the device can be connected to the sides of the chest where retractions can occur in neonates.

The device is easier to use and can be applied more quickly to a patient than other devices in the art. This makes the device more desirable for use immediately after birth than other devices. During the first minutes of life, a baby must clear the airways of fluid. This is generally done by breathing or crying efforts, which generate a negative intrapleural pressure and a negative pressure gradient which results in fluid moving from the airways into the lung interstitial space. Further, preterm babies typically cannot generate enough negative distending pressure and negative intrapleural pressure to properly clear the airways and alveoli of lung fluid. The device of the present invention can be used to stabilize the chest, allowing for more effective spontaneous breathing efforts of the diaphragm. The device can also provide "breaths" in the form of intermittent outward pulls on the anterior chest wall, for example if the baby stops breathing or when breathing is ineffective. Further, the device is easier and less-expensive to fabricate than other devices in the art because the device does not require rigid, i.e., hard plastic or metal, parts.

Figure 2:
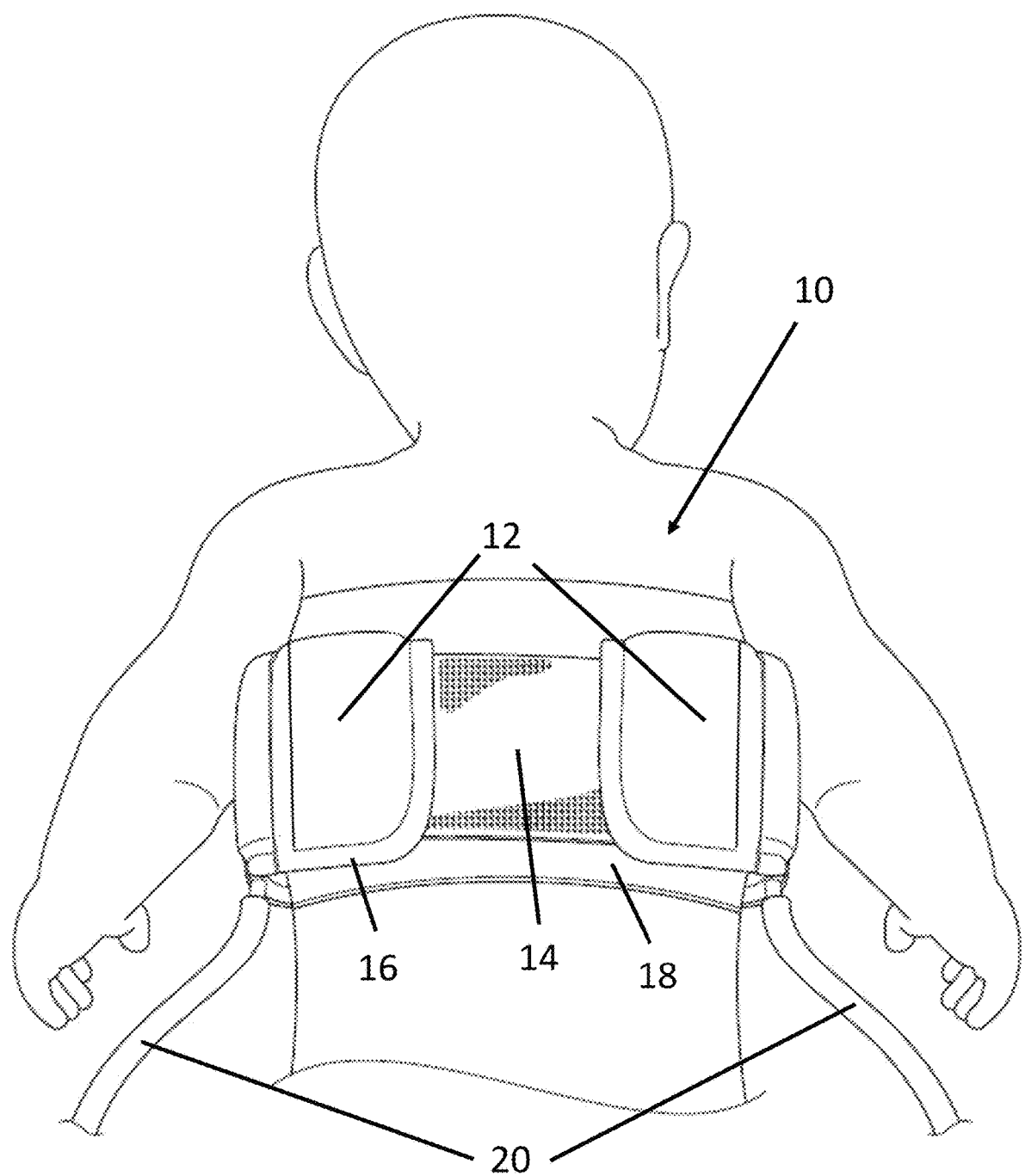
FIG. 2 is another diagram of an exemplary embodiment of the device of the present invention connected to a patient, showing a posterior view.

Referring to FIGS. 1 and 2, an exemplary embodiment of the air-splint 10 of the present invention is shown. Air-Splint 10 comprises a cuff 12 having an air bladder. In one embodiment, cuff 12 is a piece of flexible material having an inflatable compartment, wherein air can be injected into the compartment to expand the volume and/or change the shape of cuff 12. In another embodiment, cuff 12 comprises a flexible air bladder, wherein at least a portion of the air bladder is covered with a material or fabric, preferably a soft fabric or other soft material, for example moleskin, suitable for contacting a neonate's skin. In one embodiment, the material covering the air bladder, or the material the air bladder itself is made from, has fastening properties, for example, the properties of loop VELCRO.

Cuff 12 is attached to the patient's chest via an attachment mechanism. In one embodiment, the attachment mechanism comprises one or more fastening strips 14 which in turn are attached to the patient's chest. One or more fastening strips 14 can be attached to the patient's chest via an intermediary skin protective layer. In the exemplary embodiment shown, a portion of cuff 12 is attached to one side of fastening strip 14 via a fastening mechanism, in this case a VELCRO hook and loop fastener. In such an embodiment, a portion of the surface of the cuff comprises the hook or loop portion of the fastener, while the outward facing side of fastening strip 14 comprises the complementary hook or loop. Thus, cuff 12 can be readily attached to fastening strip 14. In other embodiments, cuff 12 can be connected to fastening strip 14 via any other type of fastening mechanism, as would be understood by a person skilled in the art, including, but not limited to: a snap button, clip, or buckle. The other side of fastening strip 14, i.e., the side not connected to cuff 12, is attached to the patient's skin via a skin fastener, or skin protective layer, which is described below. In one embodiment, a first fastening strip 14 is connected to the anterior portion of the patient's chest, and a second fastening strip is connected to the posterior portion of the patient's chest, i.e., the patient's back. This second fastening strip can also be connected via a skin protective layer. In such an embodiment, a first portion of cuff 12 is attached to the first fastening strip and a second portion of cuff 12 is attached to the second fastening strip, such that cuff 12 wraps around the patient's chest in a half-circle or "C" shape. In another embodiment, the cuff can comprise a more angular shape, i.e., the cuff is substantially shaped like a "7" or "L" instead of a "C." The angular shape encourages the part of the cuff over the front of the chest to lift upwards when inflated.

A tube 20, having a conduit suitable for the flow of air, is connected to cuff 12. Air can be transferred from an air source through tube 20 and into the air bladder or compartment in cuff 12, thereby inflating cuff 12. In one embodiment, a gas other than air, such as nitrogen or helium, or a liquid, can be used to inflate cuff 12. Cuff 12 is sealed to prevent air escaping from cuff 12 after it enters the cuff via tube 20. In various embodiments, the size of sealed portion 16 of cuff 12 can be any size, as would be understood by a person skilled in the art. The sealed portion of the cuff 16 forms a non-inflatable portion that can be cut as needed to fit the patient (see for example FIG. 3). In one embodiment, the width of sealed portion 16 can be sized to enable easier attachment of cuff 12 to the patient, and/or to prevent pillowing or expansion of cuff 12 where it is not required, for example in the midline on the front of the chest. By sealing the cuff as it approaches the back of the patient, that part of the cuff applied to the back is not inflated.

Figure 3:
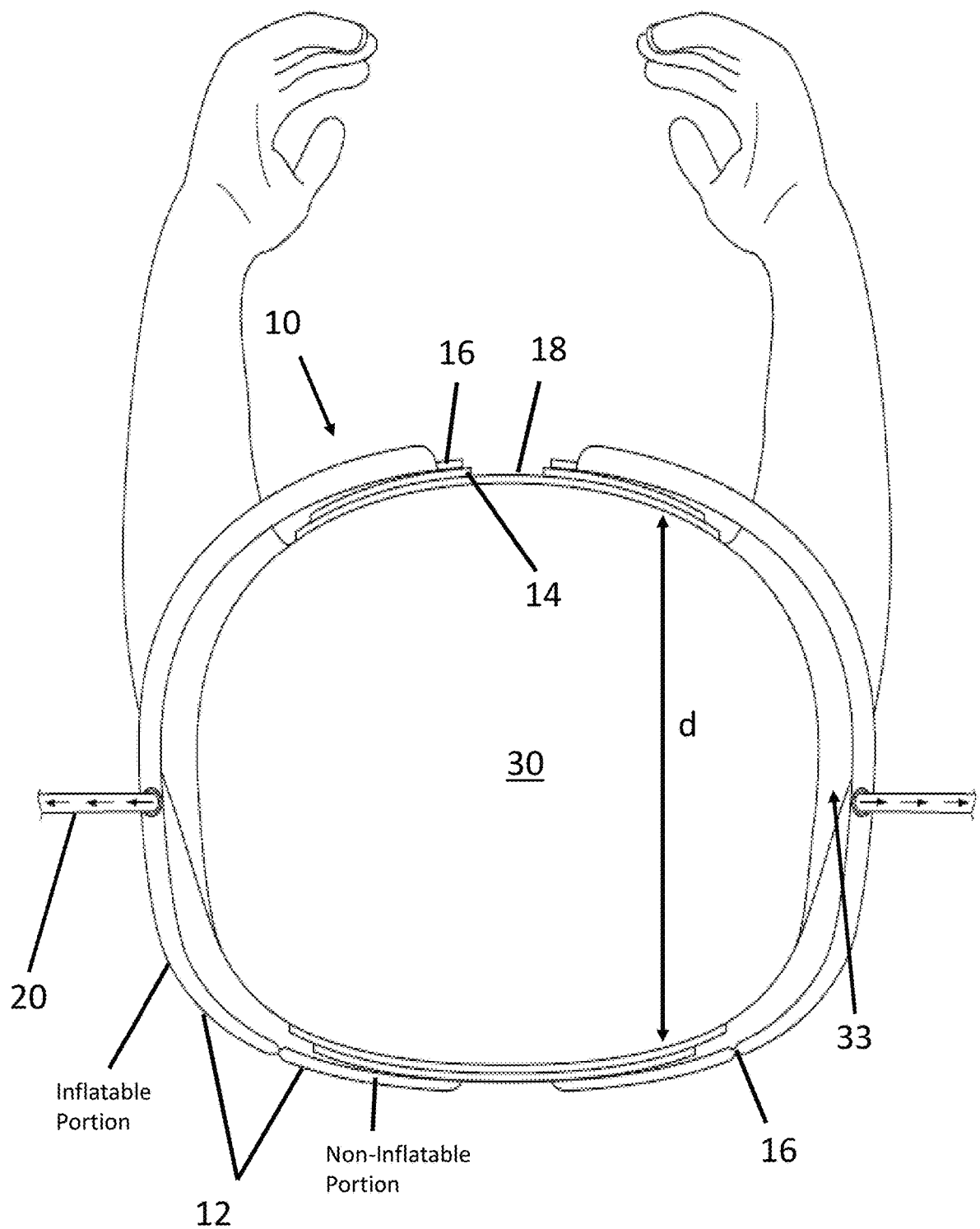
FIG. 3 is a diagram of the cross-section of an exemplary embodiment of the device of the present invention, showing a deflated cuff.
Figure 4:
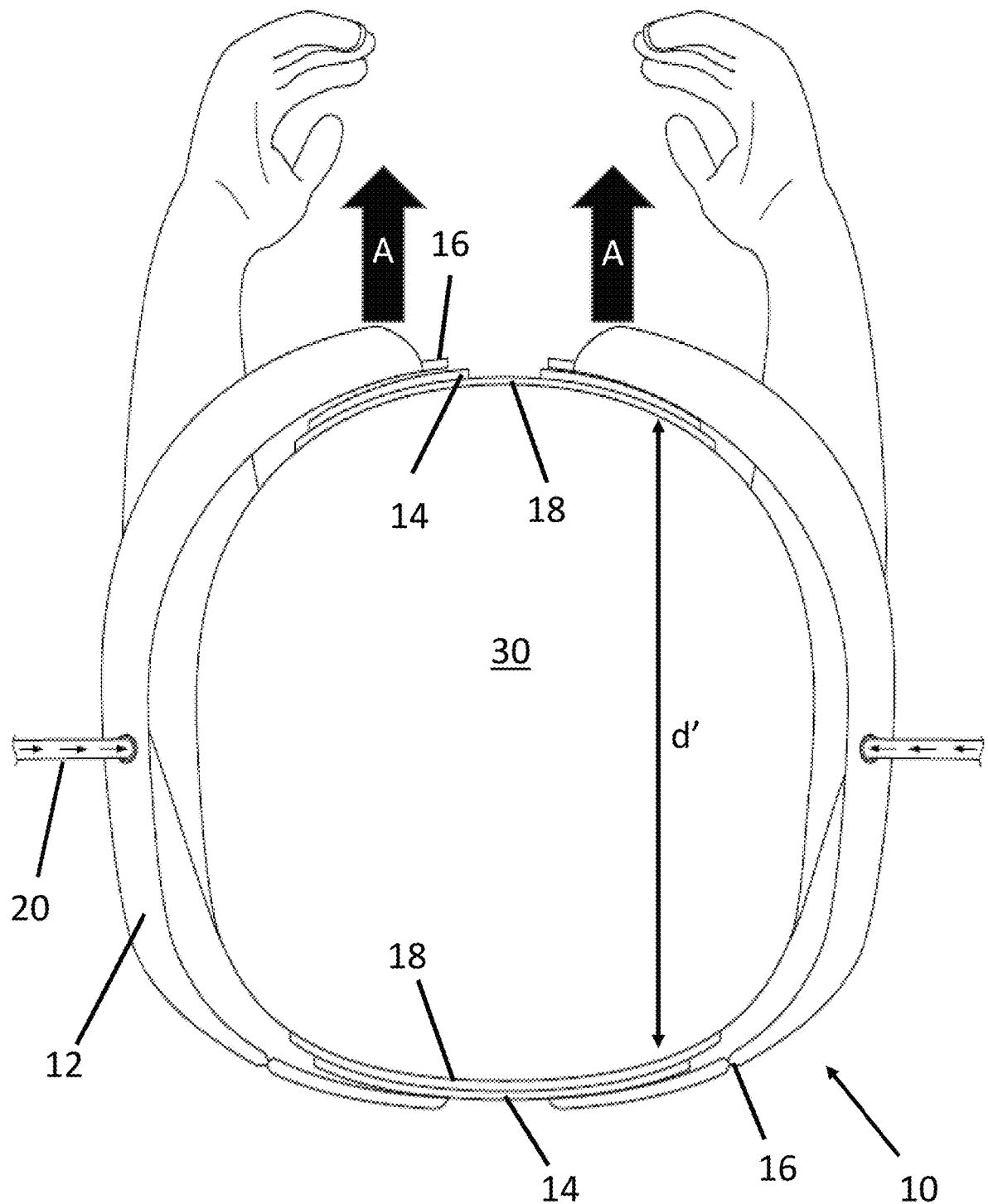
FIG. 4 is a diagram of the cross-section of an exemplary embodiment of the device of the present invention, showing an inflated cuff.

When cuff 12 is inflated, a portion of the cuff moves or extends, i.e., the cuff at least partially straightens out or otherwise changes shape, thereby applying outward force to the portion of the patient's chest that is attached to this portion of the cuff by lifting the compliant anterior section of the chest (see, for example, FIG. 3 (pre-inflation, i.e., deflated) and FIG. 4 (post-inflation, wherein the direction of the force applied by cuff 12 is shown by the arrows labeled "A")). As shown in FIGS. 3 and 4, when cuff 12 is inflated, the distance "d" corresponding to the size of the chest cavity between the anterior and posterior portions of cuff 12 is increased (i.e., the distance d can increase to a distance d'), and the sections of the patient's chest attached to these portions of cuff 12 will be expanded accordingly. Accordingly, splint 10 can assist the patient's breathing by applying outward pull to the patient's chest via cuff 12 pulling on the anterior chest wall of the patient via the connection of cuff 12 to fastening strip 14, which in turn is attached to the anterior chest wall. In a preferred embodiment, the cuff directs its outward pull to the anterior chest wall, which is the compliant section of the chest. In contrast, the posterior part of the chest wall is non-compliant and the cuff can obtain leverage by contact with the posterior-lateral aspect of the chest. In one embodiment, splint 10 is suitable sized and shaped such that the region 33 (as shown in FIG. 3) between the lateral aspect of the patient's chest wall and splint 10 is wide enough to prevent splint 10 from coming into contact with and potentially compressing the lateral aspect of the chest wall of the patient when splint 10 is inflated.

The outward pull, without compression of the side walls, causes an inhalation effect, i.e., the pulling force from the cuff causes air to enter the patient's lungs. After the bladder or compartment in cuff 12 is inflated to provide outward pull on the patient's chest, the bladder can then be deflated by removing air from the bladder, either by venting air from the bladder or by pulling vacuum on the bladder. Removing air from the bladder reduces or eliminates the outward pull on the patient's chest, thereby causing an elastic recoil of the lung and an exhalation effect, i.e., reducing or eliminating the pulling force from the cuff causes air to exit the patient's lungs. Accordingly, the splint can be used to force air into and out of the patient's lungs via the cycling of air transferred to and from the bladder in cuff 12.

In one embodiment, the cycling of air transferred to and from the bladder can be performed manually, for example by a caretaker squeezing and releasing a second bladder that is connected to tube 20, or by using a syringe to inject air and remove air from the bladder via tube 20. In another embodiment, breathing cycles can be implemented using an automated system, for example a NEOPUFF ventilation device. In such an embodiment, the NEOPUFF device can be used to provide adjustable inflating pressure to the cuff, instead of using the NEOPUFF device to ventilate the patient with a face mask or endotracheal tube. Accordingly, the splint of the present invention can be used with many types of respiratory equipment that is currently used in most neonatal intensive care units as the pressure needed to inflate the cuffs is generally within the capability of most neonatal ventilators. The device can be attached to any type of currently available ventilator or air pump with variable flow rates, and therefore does not require a specially-designed ventilator for operation. For example, one or more tubes 20 of splint 10 can be connected to any type of valve, fitting, or hose needed to connect splint 10 to the necessary respiratory equipment. In one embodiment, splint 10 can be connected to a NEOPUFF ventilation device via tubes 20. In various embodiments, the device of the present invention can comprise a port instead of tube 20, wherein the port is suitable for receiving or connecting any type of tubing, conduit, adaptor, valve, fitting, or hose, for example the hose from another device.

In one embodiment, air can be transferred to the bladder in cuff 12, where it is allowed to remain for a desired amount of time, rather than the cuff being inflated and vented in a cyclic fashion. This can be achieved by providing a continuous flow of air into the bladder or filling the bladder and sealing the air outlet. In such an embodiment, the splint can provide breathing assistance by preventing the chest wall from buckling inwards by spontaneous breathing efforts, or by correcting a subject's chest that is buckled inwards as a result of chronic collapse, e.g., pectus excurvatum, or injury. By providing a continuous outward pull on the patient's chest, a balance between elastic recoil (collapse) of the lung and the resistance of the chest wall can be maintained, thus establishing a higher lung volume with spontaneous breathing efforts than would have been achieved without the outward pull on the chest wall. When the lung is adequately inflated at rest, breathing for the patient is made easier, especially if the chest wall does not buckle inward with each breath. This is especially helpful for neonates, where even slight increases in exertion can result in respiratory fatigue and apnea and lead to the need for mechanical ventilation which is injurious to the newborn lung.

In various embodiments, the device of the present invention comprises a skin fastener, or skin protective layer, for attaching the fastening strip to the patient's skin. Referring to FIGS. 3 and 4, a cross-sectional diagram of splint 10 is shown attached to a patient's chest 30. Splint 10 comprises a cuff 12 which is connected to fastening strip 14. Fastening strip is attached to the skin of patient's chest 30 via skin fastener or skin protective layer 18. Accordingly, cuff 12 is effectively coupled with chest 30, such that when a portion of cuff 12 extends due to inflation of the bladder in cuff 12, the anterior portion of chest 30 will move with cuff 12. In one embodiment, skin fastener 18 can comprise a hydrogel or a hydrocolloid dressing, such as DUODERM, COMFEEL, or COLOPLAST hydrocolloid pectin compounds. In another embodiment, skin fastener 18 can include a semi-permeable membrane dressing, for example a thin layer of TEGADERM medical dressing. In one embodiment, the skin protective-attachment layer can be Hydrogel AG 2550C-RE-6 from Axelguard Technologies. The advantage of hydrogel is that it can be readily removed with water, thus reducing or eliminating the potential for epidermal stripping the vulnerable skin of the newly born preterm infant upon removal. In another embodiment, skin fastener 18 can be any adhesive or other type of compound suitable for contacting a patient's skin and also suitable for bonding fastening strip 14 to the patient's skin.

In one embodiment, as described herein, fastening strip 14 can be a patch that can protect the patient's skin and provide a surface for adhering the splint. In one embodiment, fastening strip 14 can include a release liner layer, a hydrogel layer, or some other type of skin protective layer, and an outer layer for adhering the splint. In such an embodiment, the release liner layer can be removed to expose the hydrogel layer for attachment to the patient's skin. Further, in such an embodiment, the outer layer can comprise a suitable material, such as polyurethane, that includes VELCRO hook attachment portions for attaching a matching VELCRO loop portion that is part of, or otherwise attached to, the splint.

In one embodiment, the cuff can be attached directly to the neonate's chest via a skin attachment mechanism. In such an embodiment, a portion of the surface of the cuff can be adapted for attachment directly to the patient's chest, whereby the cuff is attached via a hydrogel, hydrocolloid, or any other type of adhesive or skin attachment means known to a person skilled in the art. In such an embodiment, a fastening strip is not required to attach the cuff to the skin attachment mechanism.

The components of the splint of the present invention can comprise various materials. The cuff of the present invention can be made of a material that permits inflation, but preferably does not allow for excessive stretching, e.g., polyurethane. If the cuff stretches excessively, the cuff may change shape without providing the outward pull on the patient's chest that is required to provide breathing assistance to the patient. However, if the cuff is made of material that is excessively rigid, for example a metal or hard plastic, the cuff will also not provide outward pull because the cuff will not extend sufficiently during inflation. Suitable materials can be used for the surfaces of the cuff, or to reinforce the cuff so as to regulate the amount of expansion and pillowing by the cuff. The cuff can also be joined or sealed at select portions to modify the pillowing and to encourage the cuff to flex at specific points selectively. In addition, the cuff may come into contact with the patient's arm, the patient's side chest wall, or some other part of the patient's body, during operation. Accordingly, the cuff can comprise a material that reduces chaffing or irritation to the patient's skin. In one embodiment, the cuff can comprise a soft fabric such as cotton for reducing or eliminating chaffing or irritation. In another embodiment, the cuff can be coated with a material that reduces chaffing or irritation. In other embodiments, a layer of skin protective material, such as a hydrogel, hydrocolloid or other type of dressing, for example TEGADERM medical dressing, can be used to protect the patient's skin from chaffing or irritation. Other components of the splint, such as skin protective layer 18, fastening strip 14 and tube 20, can comprise any material known in the art that is useful for performing their respective functions, as would be understood by a person skilled in the art.

In one embodiment, a single L or C shaped splint of the present invention can be used to assist a patient's breathing. In another embodiment, two splints can be used, as shown in FIG. 1 and FIG. 2. In yet another embodiment, three or more splints can be used, wherein each cuff is attached to different areas of the chest. Although the device of the present invention can work suitably with a single semicircular cuff, it is more balanced and typically more effective with a cuff on both sides of the patient.

Figure 5:
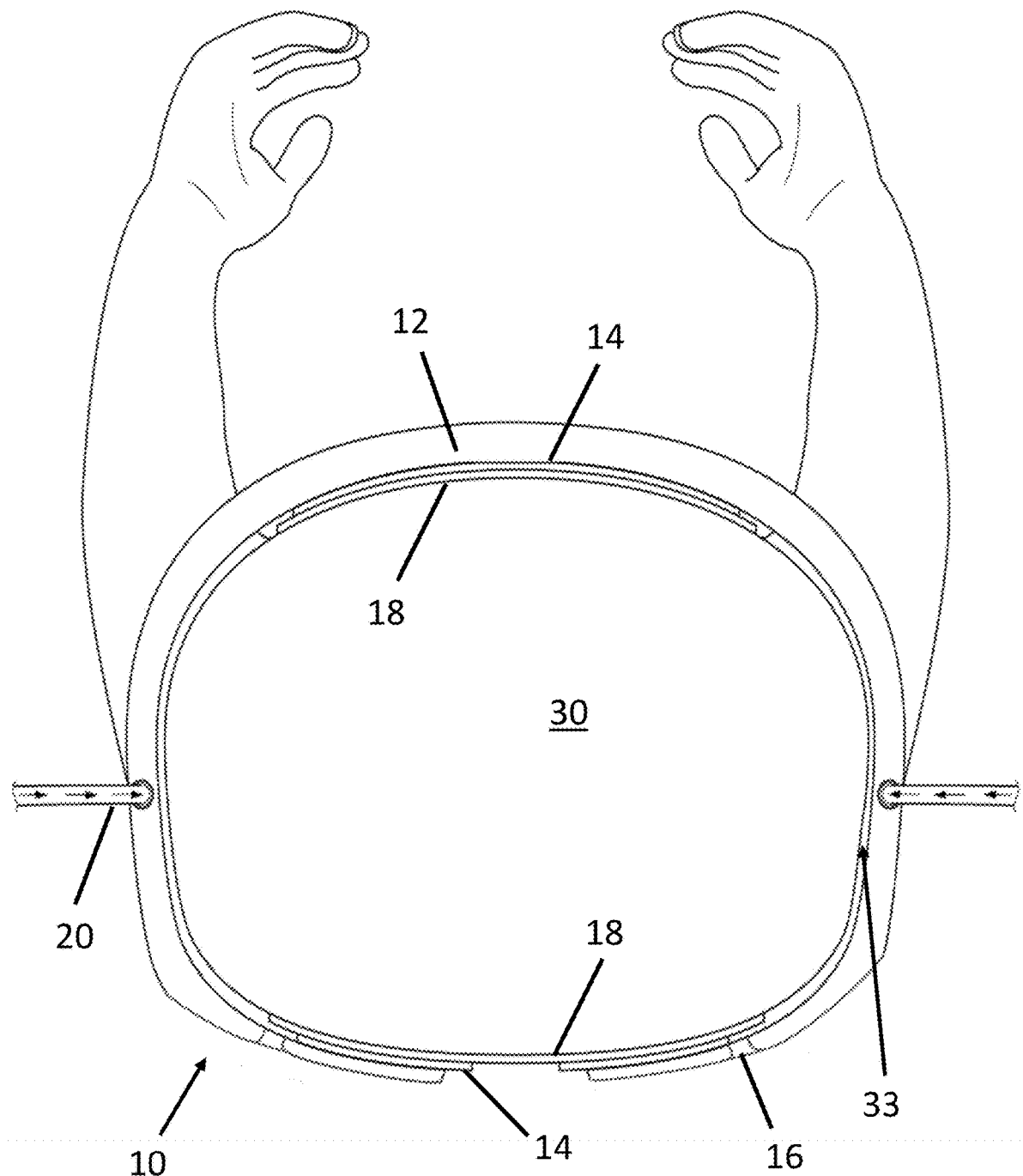
FIG. 5 is a diagram of another exemplary embodiment of the device of the present invention, having a continuous cuff over the patient's chest.

In yet another embodiment, as show in FIG. 5, if applying a compressive force on the chest is desired, then a single cuff that closely encircles the chest can be used. In one embodiment, as shown in FIG. 5, cuff 12 can completely cover the anterior portion of the chest while leaving a portion of the posterior chest uncovered. In such an embodiment, cuff 12 can also be relatively close to the lateral aspect of the patient's chest wall when inflated, i.e., such that the space between the chest wall and cuff 12 represented by region 33 is reduced or even completely eliminated, as compared to other embodiments described herein. When a cuff as shown in FIG. 5 is inflated it can encroach on the chest wall pushing it inwards and raise intrathoracic pressure. In one embodiment, to facilitate a compressive force, the skin-facing surface of the single circumferential cuff can be fabricated from a more flexible yet substantially inelastic material than the outer layer to facilitate expansion and bulging of the cuff towards the patient. In certain embodiments, to achieve the bulging of the cuff towards the chest, more material can be used to form the cuff on the side facing the patient. In one embodiment, the portion of the cuff attached to the posterior chest is not inflatable.

Accordingly, in one embodiment, splint 10 can include two cuffs 12 that are placed on the chest so that they each cover roughly half the diameter of the chest (as shown in FIGS. 1-4). When inflated this embodiment facilitates a negative distending pressure to the chest. In another embodiment, splint 10 can include only one cuff 12 that encircles most or all of the chest and is continuous over the sternum (as shown in FIG. 5). When such a single cuff is inflated it will compress the anterior portion of the chest, causing a rise in intrathoracic pressure thus facilitating exhalation.

Figure 6:
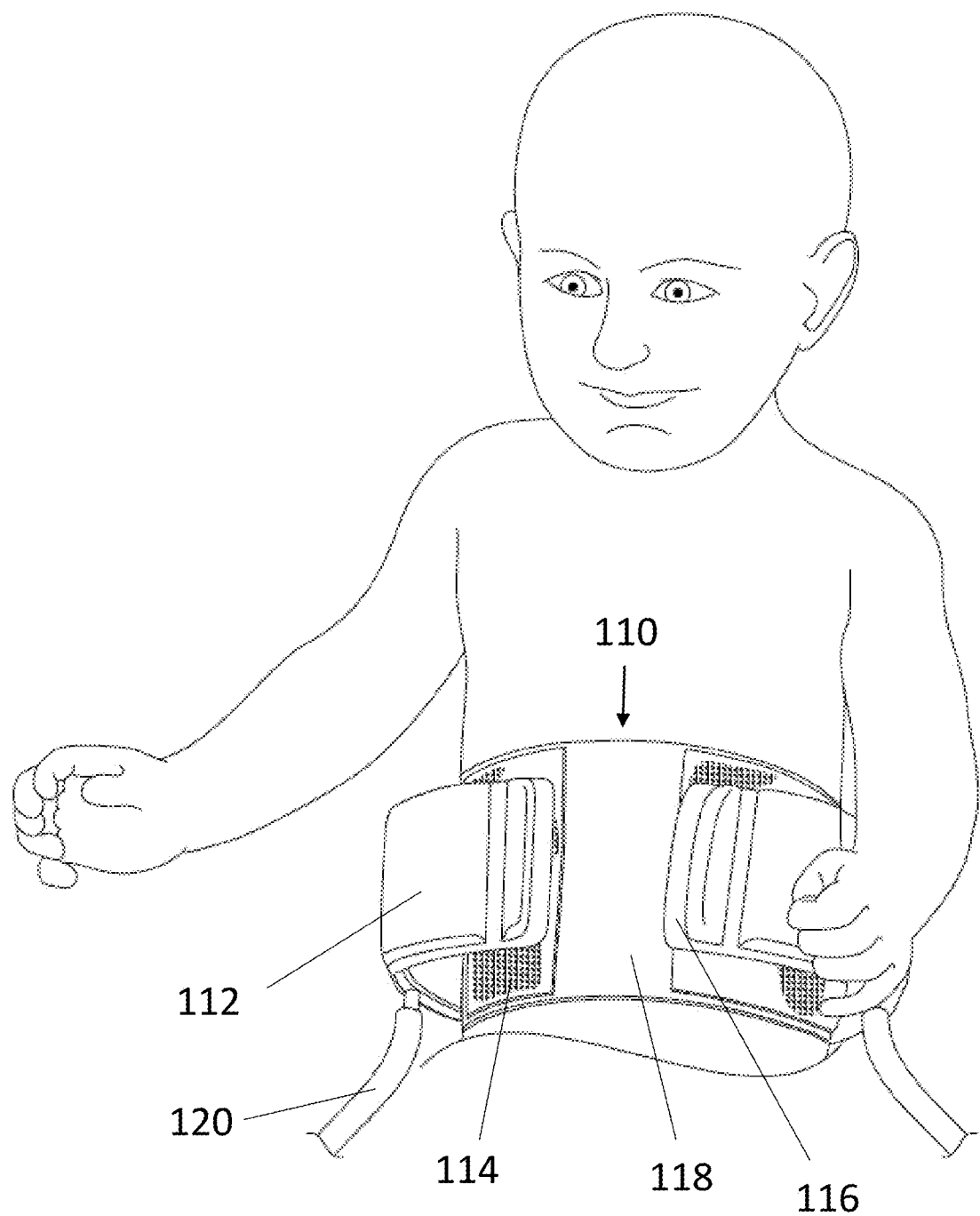
FIG. 6 is a diagram of an exemplary embodiment of the device of the present invention connected to a patient, showing an anterior view of an abdominal splint.
Figure 7:
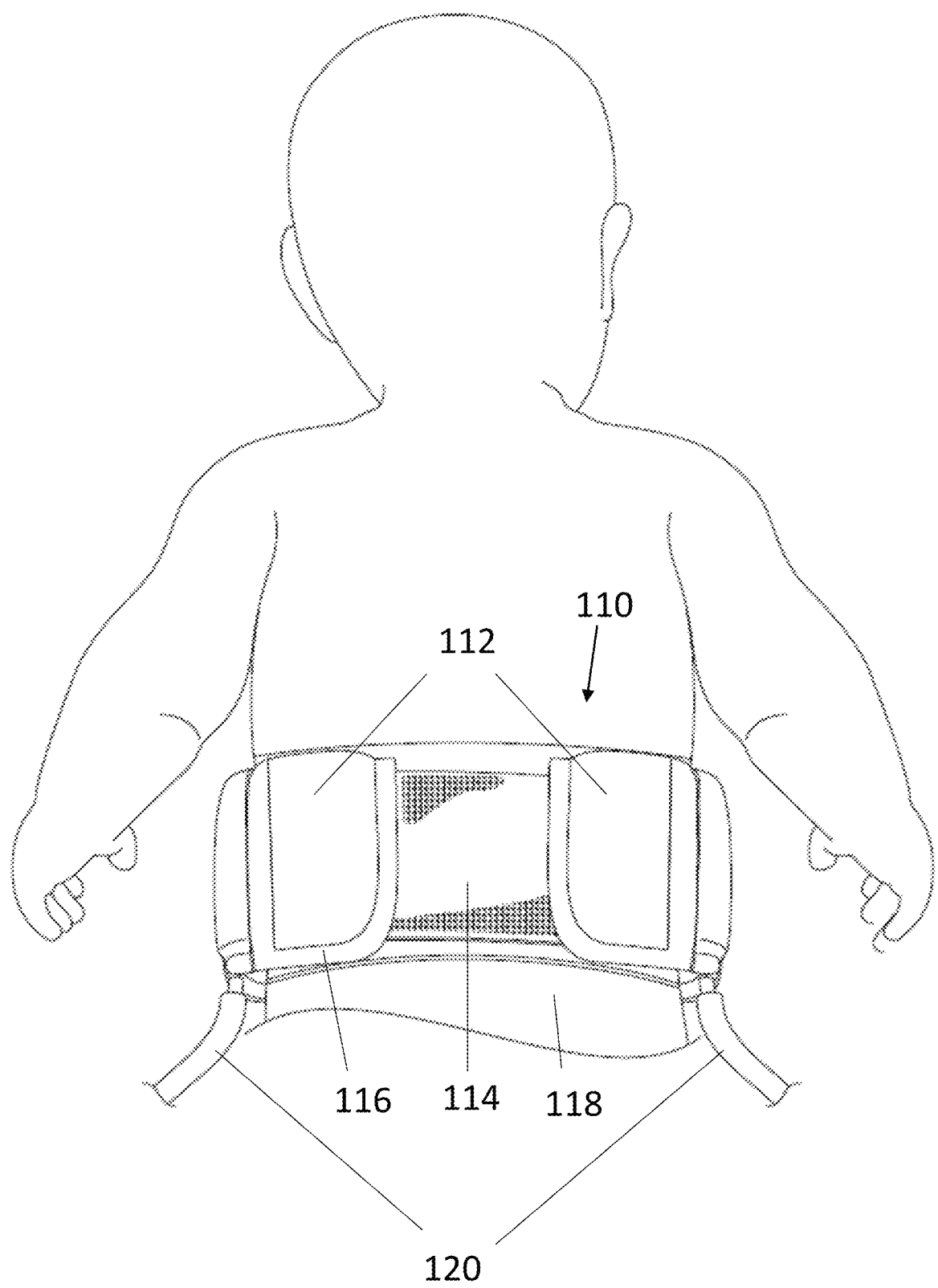
FIG. 7 is another diagram of an exemplary embodiment of the device of the present invention connected to a patient, showing a posterior view of an abdominal splint.

According to certain embodiments, an abdominal splint can be used to facilitate breathing in accordance with many of the techniques described above. The abdominal splint can be used alone instead of the splint placed on the chest (see for example FIGS. 6 and 7), or alternatively, the abdominal splint can be used in addition to the splint placed on the chest to supplement patient breathing (see for example FIGS. 8 and 9). Referring now with reference specifically to FIGS. 6 and 7, an exemplary embodiment of the abdominal splint 110 of the present invention is shown. Components of the abdominal splint 110 can operate in a similar fashion to the air splint 10 described above. In one embodiment, the abdominal splint 110 comprises a cuff 112 having an air bladder. In one embodiment, cuff 112 is a piece of flexible material having an inflatable compartment, wherein air can be injected into the compartment to expand the volume and/or change the shape of cuff 112. In another embodiment, cuff 112 comprises a flexible air bladder, wherein at least a portion of the air bladder is covered with a material or fabric, preferably a soft fabric or other soft material, for example moleskin, suitable for contacting a neonate's skin. In one embodiment, the material covering the air bladder, or the material the air bladder itself is made from, has fastening properties, for example, the properties of loop VELCRO.

Cuff 112 is attached to the patient's abdomen via an attachment mechanism. In one embodiment, the attachment mechanism comprises one or more fastening strips 114 which in turn are attached to the patient's abdomen. One or more fastening strips 114 can be attached to the patient's abdomen via an intermediary protective layer. In the exemplary embodiment shown, a portion of cuff 112 is attached to one side of fastening strip 114 via a fastening mechanism, in this case a VELCRO hook and loop fastener. In such an embodiment, a portion of the surface of the cuff comprises the hook or loop portion of the fastener, while the outward facing side of fastening strip 114 comprises the complementary hook or loop. Thus, cuff 112 can be readily attached to fastening strip 114. In other embodiments, cuff 112 can be connected to fastening strip 114 via any other type of fastening mechanism, as would be understood by a person skilled in the art, including, but not limited to: a snap button, clip, or buckle. The other side of fastening strip 114, i.e., the side not connected to cuff 112, is attached to the patient's skin via a skin fastener, or skin protective layer, which is described below. In one embodiment, a first fastening strip 114 is connected to the anterior portion of the patient's abdomen, and a second fastening strip is connected to the posterior portion of the patient's abdomen, i.e., the patient's lower back. This second fastening strip can also be connected via a skin protective layer. In such an embodiment, a first portion of cuff 112 is attached to the first fastening strip and a second portion of cuff 12 is attached to the second fastening strip, such that cuff 112 wraps around the patient's abdomen in a half-circle or "C" shape. In another embodiment, the cuff can comprise a more angular shape, i.e., the cuff is substantially shaped like a "7" or "L" instead of a "C." The angular shape encourages the part of the cuff over the front of the abdomen to lift upwards when inflated.

A tube 120, having a conduit suitable for the flow of air, is connected to cuff 112. Air can be transferred from an air source through tube 120 and into the air bladder or compartment in cuff 112, thereby inflating cuff 112. In one embodiment, a gas other than air, such as nitrogen or helium, or a liquid, can be used to inflate cuff 112. Cuff 112 is sealed to prevent air escaping from cuff 112 after it enters the cuff via tube 120. In various embodiments, the size of sealed portion 116 of cuff 112 can be any size, as would be understood by a person skilled in the art. For example, in one embodiment, the width of sealed portion 116 can be sized to enable easier attachment of cuff 112 to the patient, and/or to prevent pillowing or expansion of cuff 112 where it is not required, for example in the midline on the front of the abdomen.

When cuff 112 is inflated, a portion of the cuff moves or extends, i.e., the cuff at least partially straightens out or otherwise changes shape, thereby applying outward force to the portion of the patient's abdomen that is attached to this portion of the cuff by lifting the compliant anterior section of the abdomen (in a similar fashion as explained above with reference to FIGS. 3 and 4). Accordingly, the splint 110 can assist the patient's breathing by applying outward pull to the patient's abdomen via cuff 112 pulling on the anterior abdomen wall of the patient via the connection of cuff 112 to fastening strip 114, which in turn is attached to the anterior abdomen wall. In a preferred embodiment, the cuff directs its outward pull to the anterior abdomen wall, which is the compliant section of the abdomen. In contrast, the posterior part of the abdomen wall is non-compliant and the cuff can obtain leverage by contact with the posterior-lateral aspect of the abdomen.

Various arrangements of cuffs can be used according to the principles described herein. For example, in one embodiment, the splint has a single cuff that can be used on the left or right side of the chest or abdomen. In one embodiment, the splint has two cuffs, one positioned for use on the left side and the other positioned for use on the right side of the subject's chest or abdomen. In one embodiment, two splints each having a right and left cuff are utilized as part of a system that allows a first splint to position a first cuff on the left chest and a second cuff on the right chest, and a second splint to position a third cuff on the left abdomen and a fourth cuff on the right abdomen. In a similar embodiment, all four cuffs are positioned on a single splint. A splint according to this embodiment can be taller to accommodate all four cuffs. A taller cuff can also be utilized for example to accommodate two cuffs only on the right side (right chest, right abdomen) or only on the left side (left chest, left abdomen). In embodiments where more than one cuff are positioned on a splint, a single air source tube can be used as a central air supply, and valves controlling air flow to branches leading to each cuff can be opened and closed to individually inflate each cuff as desired. An exhaust valve can also be connected to each cuff to individually deflate each cuff as needed.

The outward pull on the abdomen, without compression of the side walls, reduces the pressure in the abdomen causing the diaphragm to move downward as it normally does during spontaneous inspiration. Displacement of the diaphragm towards the abdomen and out of the chest creates more volume and negative pressure in the chest. Of note other forms of negative pressure ventilation such as the iron lung or cuirass ventilator include the abdomen within the negative pressure environment. Therefore adding the abdominal cuffs will enhance the negative distending pressure on the lungs and enhance the effect of the chest cuffs. After the bladder or compartment in cuff 112 is inflated to provide outward pull on the patient's abdomen, the bladder can then be deflated by removing air from the bladder, either by venting air from the bladder or by pulling vacuum on the bladder. Removing air from the bladder reduces or eliminates the outward pull on the patient's abdomen, thereby causing an elastic recoil of the abdominal wall allowing the diaphragm to return to its normal position during exhalation.

Figure 8:
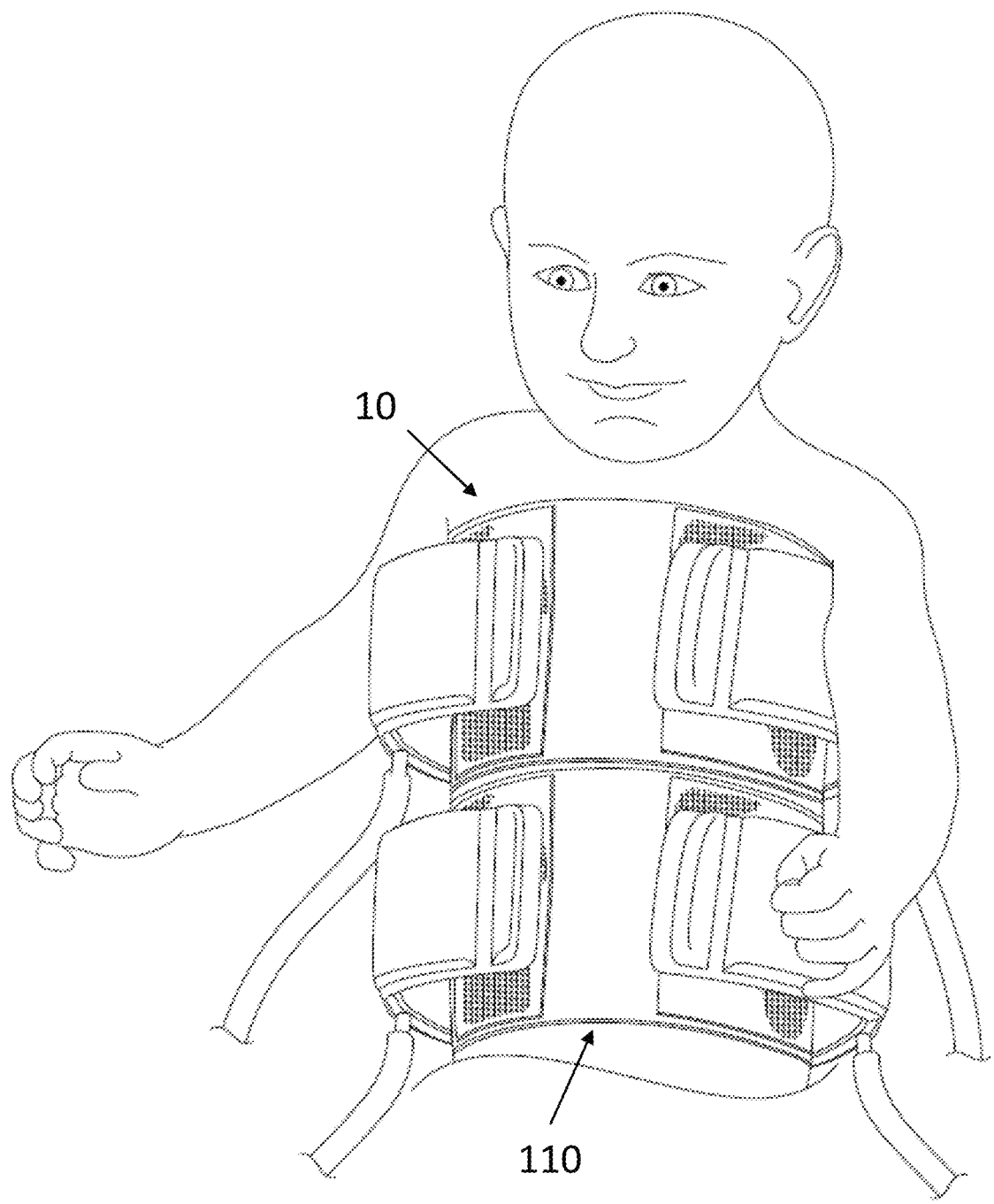
FIG. 8 is a diagram of an exemplary embodiment of the device of the present invention connected to a patient, showing an anterior view of a chest and abdominal splint.
Figure 9:
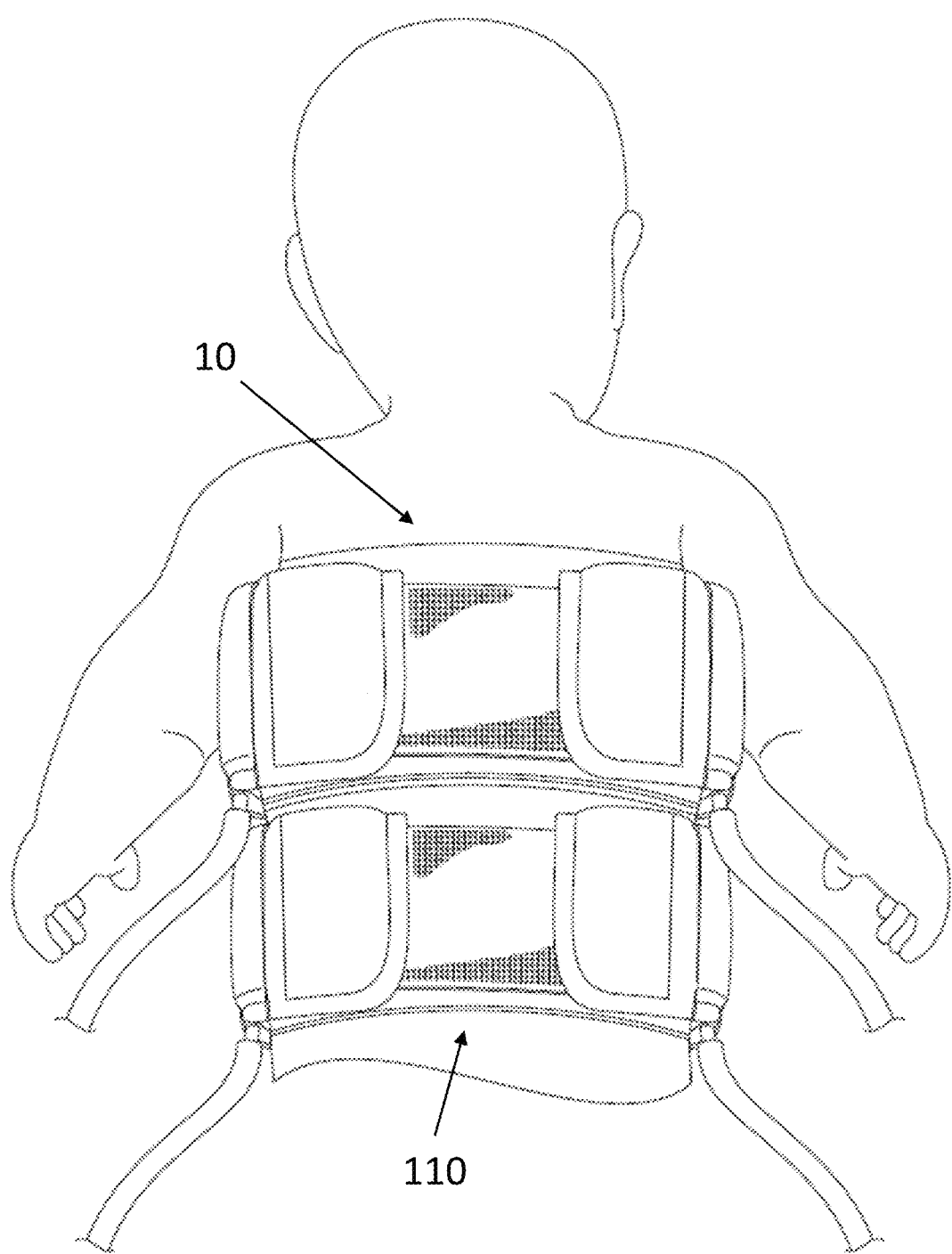
FIG. 9 is another diagram of an exemplary embodiment of the device of the present invention connected to a patient, showing a posterior view of a chest and abdominal splint.

With reference now to FIGS. 8 and 9, in certain embodiments, an abdomen splint 110 can be used in addition to the air splint 10 to support ventilation. In one embodiment, the abdomen splint 110 is adhered to the abdomen to operate in phase with an air splint 10 adhered to the chest. Sensors can be utilized in each of the abdomen splint 110 and the chest splint 10 to detect abdominal or chest movement. Detected abdomen and chest movement measurements can be communicated in a feedback loop to a control unit that changes at least one operational parameter of each splint 10, 110, for example displacement and/or phase. A controller can also be used to individually manipulate the operation of each splint 10, 110, so that for example they are in-phase, out of phase, operating at the same displacement levels, operating at different displacement levels, or are otherwise in an "on" or "off" operational state. In certain embodiments, the chest splint 10 is the primary splint used to facilitate breathing and is used in the high frequency mode, and the abdominal splint 110 only operates in synchrony with spontaneous breathing effort as detected by abdominal motion or a sensor that measures diaphragm activity. In certain embodiments, the abdominal splint 110 is the primary splint used to facilitate breathing, and the chest splint 10 only operates as needed. In certain embodiments, a controller is used to automatically switch operation between the chest splint 10 and the abdominal splint 110 based on for example breathing characteristics detected from one or more sensors, position of the patient, or to provide backup based on a failure mode detected in one of the splints.

Accordingly, the design of the cuff can influence whether a negative or positive pressure is applied to the chest wall. In addition to applying negative distending pressure, a modification of the present invention can apply a positive oscillatory compressive force to the chest wall. High frequency compressive chest wall oscillation is performed in older pediatric and adult patients with a compressive vest or cuirass. This action is used to mobilize secretions in the airway and is of great benefit for patients with cystic fibrosis. There is no current method available for providing negative or positive pressure chest wall oscillation in the small preterm infant.

When more than one splint is used, the cuffs can be attached to a single fastening strip on each side of the patient, or multiple fastening strips. As can be seen in FIGS. 1 and 2, each cuff is separate and does not connect at the front or back, however, only a single fastening strip on the anterior side and a single fastening strip on the posterior side are required to connect both cuffs to the patient. Further, when two or more splints are used, a single air tube can be connected to the air bladder of one splint, while the air bladders of the one or more additional splints are connected to each other via one or more secondary air tubes. In such an embodiment, the conduits of the secondary air tubes can allow the compartments or air bladders of each cuff to be communicatively coupled. Accordingly, in such an embodiment, the cuffs of multiple splints can be inflated by injecting air via a single air tube.

The degree of outward pull provided by the device can be adjusted based on the amount of air in the cuff. For example, the distending pressure can be controlled by increasing the amount of air added to the bladder, or by removing air from the bladder. This allows the operation of the device to be fine-tuned, allowing for relatively small, and thus safe, adjustments of negative distending pressure on the patient's chest. In various embodiments, a clinician can adjust the flow into the cuff using a flow controller so as to obtain slight chest movement and prevent over-distension of the lung. In one embodiment, the operation of the device can be fine-tuned by using a ventilation device useful for measuring air flow, such as a NEOPUFF device. When using the NEOPUFF device, a clinician can adjust the amount of continuous airway pressure delivered to the cuff instead of to a face mask or endotracheal tube. In another embodiment, the operation of the device can be controlled by using a syringe with volume indicators. In one such embodiment, the cuff can be optimally inflated with about 5 mL of air via a syringe, or a self-inflating bag with a one way valve. In another embodiment, the cuff can be inflated using airflow with pressure regulated by a connection to a tube submerged under water so the pressure delivered to the cuff would bubble of at the set height of the water column. This method of inflating the tubes can provide negative distending pressure as well as chest wall oscillations produced by the bubbles. In such an embodiment, the height of the water column can regulate the amount of inflation. In addition, the inflation of the cuff can be synchronized with spontaneous breathing by the patient, as detected by abdominal movement, or mechanical or electrical detection of diaphragmatic movement, i.e., NAVA ventilation. In one embodiment, the device of the present invention can be used in conjunction with a MAQUET SERVO-i ventilator. In one embodiment, the abdominal movement is detected by one or more sensors positioned on an abdominal splint.

The present invention also comprises various methods for providing breathing assistance in a neonate. In one embodiment, the present invention is a method for assisting breathing in a neonate comprising the steps of: attaching a cuff having an inflatable compartment to the chest of a neonate and inflating the cuff by transferring air into the compartment, thereby applying negative distending pressure to the neonate's chest via the action of the cuff being extended and pulling the neonate's chest outward. The method may further comprise the step of at least partially deflating the cuff to reduce the negative distending pressure applied to the neonate's chest. In one embodiment, a portion of the neonates' chest, preferably the sternum, is not covered by the cuff. In one embodiment, more than one cuff can be used at the same time to cover multiple regions of the neonate's chest. In another embodiment, a single cuff that encircles the chest can be used to apply a compressive force on the chest wall.

In other embodiments, the cuff of the present invention can be extended via a mechanism other than an air bladder. For example, in one embodiment, the cuff can comprise a piezoelectric material instead of an air bladder, wherein the shape of the cuff can be changed in response to an electrical signal. In such an embodiment, the cuff can be attached to the chest and back of a subject similarly to the other embodiments of the device described herein. The cuff can then be extended by applying an electrical signal to the piezoelectric material, thereby providing negative distending pressure to the subject. Further, in such an embodiment, the device can be controlled by a microprocessor, wherein breathing cycles can be provided to the subject via a cycling of the electrical signal applied to the piezoelectric material. In another embodiment, the cuff can comprise both a piezoelectric material and an air bladder. In one such embodiment, the air bladder can be used to provide continuous negative distending pressure and/or to provide optimal fit of the cuff to the patient, while the piezoelectric material can be used to change the shape of the cuff. For example, in such an embodiment, the piezoelectric material can be pulsed intermittently to provide breathing cycles to the patient.

Experimental Examples

An exemplary embodiment of the air-splint similar top that shown in FIGS. 1-4 was used on a suitable mannequin with chest dimension similar to a 0.8 kg infant. The mannequin had an endotracheal tube placed through the mouth into the hollow thoracic cavity. The tube provided the only access to the thoracic cavity, which was otherwise sealed where the diaphragm was situated. The air-splint was sized to correspond to the dimensions of a typical 0.8 kg preterm infant. In other embodiments, the air-splint can be sized for the dimensions of an infant in the range of 500-4000 grams. However, the air-splint is not meant to be limited to any specific shape or size described herein, and can be any shape or size as would be understood by a person skilled in the art.

Figure 10:
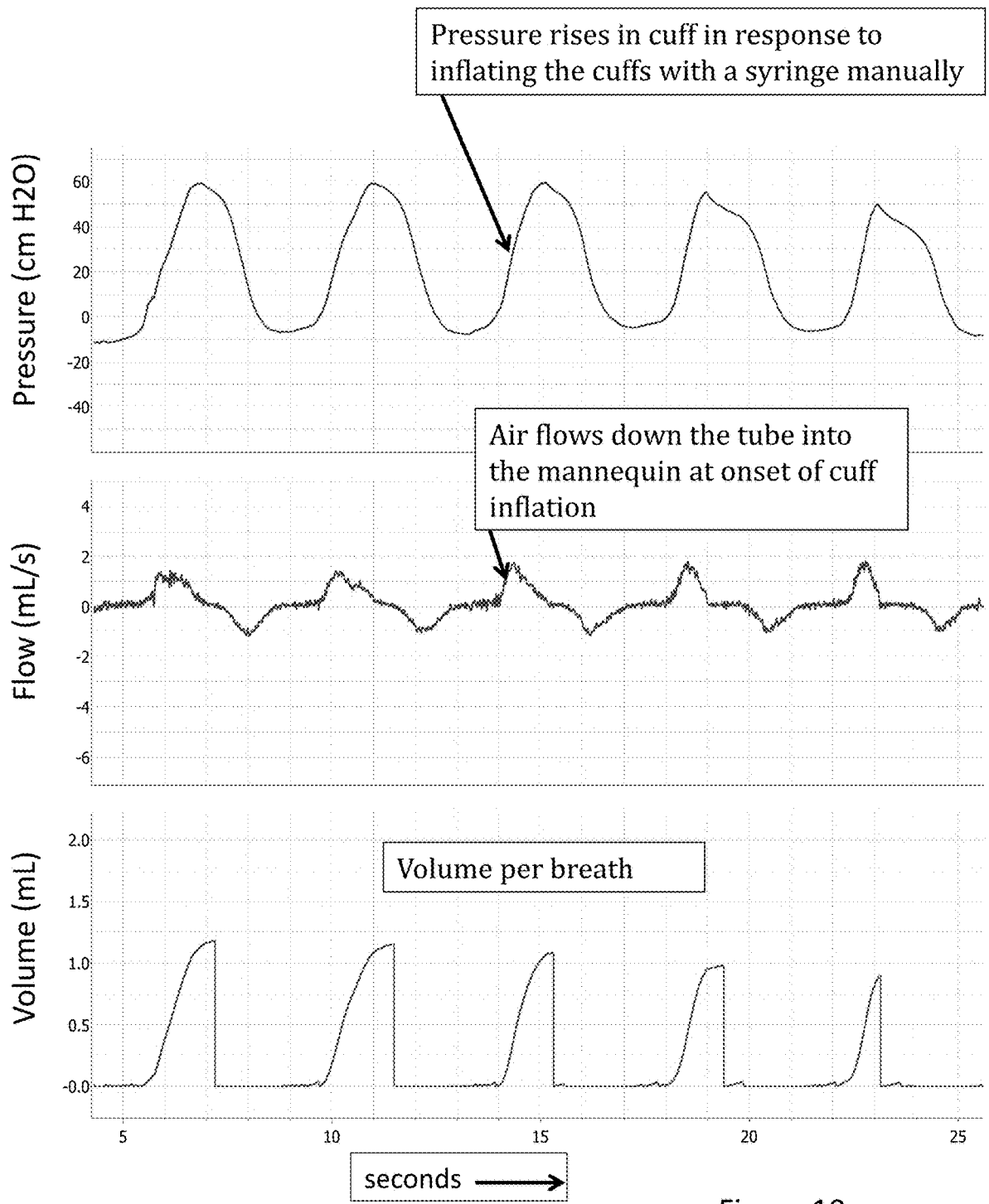
FIG. 10 is a graph showing pressure, flow and volume data over time from the experimental testing of an exemplary embodiment of a pair of cuffs on the chest. The test mannequin had the dimensions of 0.8 kg infant. Accordingly the volume of air drawn into the chest with each inflation of the cuff represents approximately 30% of a normal tidal volume.

Ventilation was simulated on the mannequin by inflating the cuffs with a syringe. Enough pressure was generated to inflate the cuffs so that the anterior chest wall rise could be observed. As the chest cavity of the mannequin was sealed, when the chest wall rose, air flowed into the endotracheal tube. The flow down the endotracheal tube of the mannequin and the pressure in the cuffs was measured and recorded with a Hans Rudolph pneumotach, amplifier, and Powerlab data acquisition system (see FIG. 10). The volume of air delivered in these "breaths" was approximately 1.2 ml which represents about 30% of a normal tidal volume for this size infant No appreciable delay between the rise in pressure in the cuffs and the start of flow into the chest via the endotracheal tube was observed. This is important as it shows that the cuffs can be used to deliver flow synchronized to the inspiratory cycle of the infant without delay. This can be clinically relevant as the glottis is open during inspiration and closed on expiration. The volume of air moved is more than sufficient for high frequency ventilation that can be achieved with very low tidal volumes. The volume is also sufficient to be a clinically relevant augmentation of normal tidal volume breaths The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A splint for assisting breathing in a subject, comprising:
a first flexible cuff having an inflatable compartment;
a tube connected to the inflatable compartment of the first cuff, wherein the tube is suitable for delivery or removal of air from the compartment; and
an attachment mechanism configured to engage the first cuff to a region of the subject's chest or abdomen,
wherein the first cuff is configured to attach to a chest or abdomen of the subject and a posterolateral or posterior region of the subject via the attachment mechanism, and when the inflatable compartment is in an inflated state, a portion of the first cuff is configured to extend and apply a negative distending pressure to the subject's chest or abdomen, and when the inflatable compartment is in a deflated state, the first cuff is configured to eliminate all application of negative distending pressure applied to the subject's chest or abdomen by the splint.

2. The splint of claim 1 further comprising:
a second flexible cuff having a second inflatable compartment,
a second tube connected to the second inflatable compartment of the second cuff, wherein the second tube is suitable for delivery or removal of air from the second compartment; and
an attachment mechanism configured to engage the second cuff to a region of the subject's chest or abdomen,
wherein when the second cuff is attached to a chest or abdomen of the subject and a posterolateral or posterior region of the subject via the attachment mechanism and the compartment is inflated, a portion of the second cuff is configured to extend and apply a negative distending pressure to the subject's chest or abdomen.

3. The splint of claim 2, wherein the first cuff is configured for attachment to a left side of the subject, and wherein the second cuff is configured for attachment to a right side of the subject.

4. The splint of claim 2, wherein both the first and second cuffs are configured for attachment to a same side of the subject.

5. A splint system comprising:
the splint of claim 2, wherein the splint of claim 2 is a first splint; the first flexible cuff and the second flexible cuff of the first splint are designated for attachment to the chest of the subject; a second splint comprising a third flexible cuff and a fourth flexible cuff, wherein the third flexible cuff and the fourth flexible cuff of the second splint are designated for attachment to the abdomen of the subject.

6. The system of claim 5 further comprising:
a controller operably connected to the first splint and the second splint.

7. The system of claim 6 further comprising:
at least one sensor;
wherein the controller is configured to change operation of the first splint and the second splint based on feedback detected from the at least one sensor.

8. The system of claim 7, wherein the change in operation is at least one of synchronization, displacement, or an on/off operational state.

9. The splint of claim 1, wherein the splint is flexible and inelastic.

10. The splint of claim 1, wherein the attachment mechanism comprises one or more fastening strips, a means for attaching the one or more fastening strips to the subject's skin, and a means for attaching the one or more fastening strips to the cuff.

11. The splint of claim 10, wherein the means for attaching the one or more fastening strips to the cuff is a hook and loop fastener.

12. The splint of claim 10, wherein the means for attaching the one or more fastening strips to the subject's skin comprises a hydrogel, a hydrocolloid dressing, or a semipermeable membrane.

13. The splint of claim 1 further comprising:
a syringe or a bulb syringe configured to transfer air to and inflate the compartment.

14. The splint of claim 1 further comprising:
a ventilator or an air pump configured to transfer air to and inflate the compartment.

15. The splint of claim 1, wherein the splint is configured to avoid covering the subject's sternum when the splint is attached to the subject.

16. The splint of claim 1, wherein at least a portion of a surface of the cuff comprises a soft fabric.

17. The splint of claim 1, wherein the first cuff is configured to provide an air gap separating and immediately adjacent to the chest or abdomen and the first cuff.

18. A method for assisting breathing in a subject comprising the steps of:
attaching a splint having at least one flexible cuff having an inflatable compartment to the chest or abdomen and a posterolateral or posterior region of a subject;
inflating the at least one cuff by transferring air into the compartment; and
applying a negative distending pressure to the subject's chest or abdomen via the inflating;
when the inflatable compartment is in a deflated state, the at least one cuff is configured to eliminate all application of negative distending pressure applied to the subject's chest or abdomen by the splint.

19. The method of claim 18, further comprising:
at least partially deflating the at least one cuff to reduce the negative distending pressure applied to the subject's chest or abdomen.

20. The method of claim 18, wherein at least a portion of the subject's chest or abdomen is not covered by the at least one cuff.

21. The method of claim 20, wherein the at least a portion of the subject's chest or abdomen comprises the subject's sternum.

22. The method of claim 18, wherein the at least one cuff is attached to the subject's chest or abdomen by a skin attachment mechanism.

23. The method of claim 22, wherein the skin attachment mechanism is a hydrogel.

24. The method of claim 22, wherein the skin attachment mechanism is a hydrocolloid.

25. The method of claim 22, wherein the skin attachment mechanism is a semi-permeable membrane dressing.

26. The method of claim 18, wherein air is transferred into the compartment via a syringe or a bulb syringe.

27. The method of claim 18, wherein air is transferred into the compartment via a ventilator or an air pump.

28. The method of claim 18, wherein a predetermined amount of air is transferred into the compartment to inflate the at least one cuff.

29. The method of claim 28, wherein the predetermined amount of air corresponds to an application of negative distending pressure to the subject's chest or abdomen that causes the subject to inhale a breath approximately equal to or less than a tidal volume.

30. The method of claim 18, wherein the inflation of the at least one cuff is synchronized with the spontaneous inspiration of the subject.

31. The method of claim 18, wherein the negative distending pressure applied to the subject's chest or abdomen is maintained for a predetermined period of time.

32. The method of claim 18, further comprising the step of deflating the at least one cuff to release the negative distending pressure.

33. The method of claim 32, wherein the inflating or deflating of the at least one cuff occurs at a frequency between 2 Hz and 15 Hz and is controlled via a high frequency generator of air pressure as is found in a high frequency oscillator or a high frequency jet ventilator.

34. The method of claim 32, wherein the inflating or deflating of the at least one cuff is controlled based on the activity of the subject's diaphragm.

35. The method of claim 18, wherein the air is transferred into the compartment via a column of bubbling water set to an adjustable depth to regulate the pressure delivered to the cuff.

36. The method of claim 18 further comprising:
attaching the at least one cuff to the left side of the subject's chest and attaching a second cuff to the right side of the subject's chest.

37. The method of claim 18 further comprising:
attaching the at least one cuff to the left side of the subject's abdomen and attaching a second cuff to the right side of the subject's abdomen.

38. The method of claim 18 further comprising:
attaching the at least one cuff to the subject's chest and attaching a second cuff to the to the subject's abdomen, wherein both the at least one cuff and the second cuff are on a same side of the subject.

39. The method of claim 18 further comprising:
attaching the at least one cuff and a second cuff to the subject's chest; and
attaching a third and fourth cuff to the subject's abdomen.

40. The method of claim 18, wherein the operation of the at least one cuff is based on sensor feedback.

41. The method of claim 18 further comprising:
attaching the at least one flexible cuff to the chest or abdomen of the subject in a deflated state and without an application of a negative distending pressure.

42. A method for assisting exhalation of breathing in a subject comprising the steps of:
attaching a splint having a flexible cuff having an inflatable compartment to the chest or abdomen of a subject, wherein the cuff is continuous over the anterior portion of the subject's chest or abdomen, and
inflating the cuff by transferring air into the compartment, wherein when the inflatable compartment of the cuff is inflated the cuff compresses the chest or abdomen;
wherein when the inflatable compartment is in a deflated state, the cuff is configured to eliminate all application of negative distending pressure applied to the subject's chest or abdomen by the splint.

43. The method of claim 42 further comprising:
attaching the flexible cuff to the chest or abdomen of the subject in a deflated state and without all application of a negative distending pressure.

* * * * *